(12) United States Patent
Wolske et al.

(10) Patent No.: US 8,591,231 B1
(45) Date of Patent: Nov. 26, 2013

(54) AIR/GAS DRIVEN PROPHYLAXIS PREPARATION DISPENSING SYSTEM FOR A DENTAL HAND PIECE

(76) Inventors: Edwin W. Wolske, Alamo, CA (US); Rick T. Cole, Whitmore, CA (US)

(*) Notice: Subject to any disclaimer, the term of this patent is extended or adjusted under 35 U.S.C. 154(b) by 0 days.

(21) Appl. No.: 13/355,350

(22) Filed: Jan. 20, 2012

Related U.S. Application Data (60) Provisional application No. 61/550,974, filed on Oct. 25, 2011.

(51) Int. Cl.
*A61C 3/06* (2006.01)
*A61C 1/08* (2006.01)
*A61C 1/12* (2006.01)

(52) U.S. Cl.
USPC .......................... 433/125; 433/126; 433/133

(58) Field of Classification Search
USPC ........... 433/80, 82–85, 88–89, 124–126, 133, 433/141–142, 166, 29; 285/122.1, 120.1, 285/133.4, 188
See application file for complete search history.

(56) References Cited

U.S. PATENT DOCUMENTS

| | | | | |
|---|---|---|---|---|
| 2,400,912 A | * | 5/1946 | Britt et al. | 433/82 |
| 3,389,468 A | * | 6/1968 | Lewis et al. | 433/80 |
| 3,691,636 A | | 9/1972 | Deuschle | |
| 3,740,853 A | | 6/1973 | Brahler | |
| 3,775,849 A | * | 12/1973 | Condon | 433/87 |
| 3,798,777 A | * | 3/1974 | Reiter | 433/125 |
| 3,869,877 A | | 3/1975 | Brahler | |
| 3,987,550 A | * | 10/1976 | Danne et al. | 433/84 |
| 4,403,956 A | * | 9/1983 | Nakanishi | 433/29 |
| 4,533,324 A | | 8/1985 | Nakanishi | |
| 4,929,180 A | | 5/1990 | Moreschini | |
| 5,040,978 A | | 8/1991 | Falcon et al. | |
| 5,062,796 A | * | 11/1991 | Rosenberg | 433/82 |
| 5,209,658 A | | 5/1993 | Brahler | |
| 5,308,242 A | * | 5/1994 | McLaughlin et al. | 433/114 |
| 5,340,310 A | | 8/1994 | Bifulk | |
| 5,352,119 A | | 10/1994 | Sakurai | |
| 5,374,189 A | | 12/1994 | Mendoza | |
| 5,380,202 A | | 1/1995 | Brahler | |
| 5,482,461 A | | 1/1996 | Yale | |
| 5,507,644 A | | 4/1996 | Kivlighan, Jr. | |
| 5,571,012 A | | 11/1996 | Witherby et al. | |
| 5,642,994 A | | 7/1997 | Chipian et al. | |

(Continued)

OTHER PUBLICATIONS

Ari Katz, et al.; Auto-Dispensing Prophy Angle; Capstone Design Program: Mechanical Engineering; Jan. 28, 2008; pp. 1-45, Northeastern University Boston, MA 02115.

*Primary Examiner* — Yogesh Patel
(74) *Attorney, Agent, or Firm* — Dennis A. DeBoo (57) ABSTRACT

Air/gas driven prophylaxis preparation dispensing system coupled to a dental hand piece, the system comprising a hand piece connector receiving an air/gas pressure and adjustably diverting a portion of the air/gas pressure to drive a piston toward an open delivery end of a container containing a prophylaxis preparation for dispensing the prophylaxis preparation out of an open delivery end of the container, through a passageway surmounting a disposable prophy angle supporting a gear train, through a portion of the gear train supporting a prophy cup, through an opening in the prophy cup to an internal cavity of the prophy cup while simultaneously driving an air/gas driven rotational member of the dental hand piece coupled to the gear train with the remaining portion of the air/gas pressure to impart rotation of the prophy cup while simultaneously dispensing the prophylaxis preparation into the internal cavity thereof.

12 Claims, 8 Drawing Sheets

(56) References Cited

U.S. PATENT DOCUMENTS

| | | |
|---|---|---|
| 5,730,595 A | 3/1998 | Bailey |
| 5,733,117 A * | 3/1998 | Coss et al. ............. 433/85 |
| 5,743,718 A | 4/1998 | Mendoza et al. |
| 5,871,353 A | 2/1999 | Pierce et al. |
| 5,902,107 A | 5/1999 | Lowell |
| 6,083,000 A * | 7/2000 | Charlton ............. 433/82 |
| 6,099,309 A | 8/2000 | Cardarelli |
| 6,168,433 B1 | 1/2001 | Hamlin |
| 6,182,911 B1 * | 2/2001 | Hanks et al. ............. 239/318 |
| 6,203,322 B1 | 3/2001 | Kraenzle |
| 7,029,278 B2 * | 4/2006 | Pond ............. 433/125 |
| 7,101,182 B2 | 9/2006 | Garrison et al. |
| 7,160,108 B2 | 1/2007 | Jaffe |
| 7,255,559 B2 | 8/2007 | Shen et al. |
| 7,338,285 B1 | 3/2008 | Balaban |
| 7,422,433 B2 | 9/2008 | Carron et al. |
| 2004/0202980 A1 * | 10/2004 | Policicchio ............. 433/88 |
| 2006/0246395 A1 | 11/2006 | Pond |
| 2006/0292522 A1 | 12/2006 | Lees et al. |
| 2008/0026343 A1 | 1/2008 | Doenges et al. |
| 2008/0064007 A1 | 3/2008 | Carron et al. |
| 2009/0081610 A1 | 3/2009 | Hayman et al. |
| 2009/0098505 A1 * | 4/2009 | Randolph ............. 433/82 |

* cited by examiner

AIR/GAS DRIVEN PROPHYLAXIS PREPARATION DISPENSING SYSTEM FOR A DENTAL HAND PIECE

CROSS-REFERENCE TO RELATED APPLICATIONS

This application claims priority under 35 USC Section 119(e) to co-pending U.S. Provisional Patent Application No. 61/550,974, filed Oct. 25, 2011, the entire disclosure of which is incorporated herein by reference.

FIELD OF THE INVENTION

This invention relates generally to a dental prophylaxis system and, in particular, to an air/gas driven prophylaxis preparation dispensing system for attaching to a dental hand piece.

BACKGROUND OF THE INVENTION

In general, cleaning a patient's teeth is accomplished using a dentifrice or prophylaxis preparation applied via a right angle dental attachment operatively coupled to a standard dental hand piece. Currently, a disposable prophy angle is employed for the right angle attachment in an effort to solve the problems of transmitting fluid borne diseases between subsequent patients as well as reducing costs associated with sterilization. The prophy angle supports a prophy cup at one end and rotates the prophy cup through a system of gears disposed within the prophy angle. In turn, the system of gears is driven via a shaft which extends out of the other end of prophy angle and which is operatively coupled between the gears and a pneumatically actuated motor in the hand piece.

In operation, the rotating prophy cup of the prophy angle is used to apply the dentifrice preparation to the patient's teeth during the prophylaxis procedure for removing accumulated plaque, tartar and stain off the teeth. The dentifrice preparation is typically carried to the teeth by first dipping the prophy cup into a nearby, sometimes finger worn, individual container of the dentifrice preparation, scooping out a desired amount of the dentifrice preparation therefrom, and placing dentifrice filled prophy cup into the patient's mouth. Once therein, the motor is pneumatically actuated and the rotating prophy cup containing the dentifrice preparation is placed onto and moved along the teeth thereby resulting in the dentifrice preparation dissipating and invariably forming a slurry like substance with the patient's saliva and sometimes blood and tissue particles which migrates or attaches along the surface of the rotating cup from which it is flung into the surrounding environment as contaminated splatter. When the cup is within the patient's mouth, the contaminated splatter is typically contained. However, during this prophylaxis procedure the cup is repeatedly stopped, removed from the patient's mouth, dipped into the nearby, sometimes finger worn, individual container of dentifrice preparation for scooping out a further amount of the dentifrice preparation, carried back to the teeth, and then restarted.

This repeated procedure is not only laborious and time-consuming, but often results in the contaminated splatter being randomly flung from the cup onto the patient, the operator (e.g., the dentist, dental hygienist, or dental assistant), and the nearby equipment as a result of the cup not being completely stopped before being removed from within the patient's mouth or being prematurely started prior to being reinserted back into the patient's mouth.

As a result, problems still exist relating to the application of dentifrice preparation to a patient's teeth using an existing disposable prophy angle.

Accordingly, there is a need for a dental prophylaxis system that, inter alia, overcomes the significant shortcomings delineated hereinabove.

BRIEF SUMMARY OF THE INVENTION

Accordingly, and in one aspect, an embodiment of the invention ameliorates or overcomes one or more of the significant shortcomings of the known prior art by providing an air or gas driven prophylaxis preparation dispensing system for attaching to a dental hand piece.

More specifically, and in one aspect, an embodiment of the invention provides an air/gas driven prophylaxis preparation dispensing system for attaching to a dental hand piece having an air/gas driven rotational member, said system comprising: (1) a disposable prophy angle comprised of a housing operatively supporting a gear train, said gear train having a posterior end removably attached to an air/gas driven rotational member of a dental hand piece to impart rotation of said gear train, and said gear train having a ventral end removably attached to a superior portion of a prophy cup, said prophy cup having a medial portion inferiorly transitioning into an outer peripheral wall having an inner surface defining an inner cavity, said medial portion having an opening extending therethrough and in open communication with said inner cavity of said prophy cup; (2) a prophylaxis preparation receptacle superiorly mounted on said disposable prophy angle, said prophylaxis preparation receptacle having an open posterior end; (3) a passageway in open communication with said open posterior end of said prophylaxis preparation receptacle and extending through said prophylaxis preparation receptacle, a superior portion of said housing, and a portion of said gear train to said opening in said medial portion of said prophy cup wherein said passageway provides open communication between said prophylaxis preparation receptacle and said inner cavity of said prophy cup; (4) a prophylaxis preparation container having a cavity containing a prophylaxis preparation and having an open entrance end and an opposing open delivery end in open communication with said cavity; (5) a free piston disposed within said cavity between said open entrance end and said prophylaxis preparation; (6) a prophylaxis preparation outlet tube operatively coupled between said open delivery end of said prophylaxis preparation container and said open posterior end of said prophylaxis preparation receptacle for providing open communication between said cavity containing the prophylaxis preparation and said passageway; (7) receiving and diverting means for receiving an air/gas pressure and adjustably diverting a portion of the air/gas pressure to drive said free piston toward said open delivery end of said prophylaxis preparation container for dispensing said prophylaxis preparation out of said open delivery end, through said prophylaxis preparation outlet tube and said passageway, and out of said opening extending through said medial portion of said prophy cup to said internal cavity of said prophy cup while simultaneously driving said air/gas driven rotational member of said dental hand piece with a remaining portion of the air/gas pressure to impart rotation of said prophy cup while simultaneously dispensing the prophylaxis preparation into said internal cavity of said prophy cup.

In another aspect, an embodiment of the invention provides an air/gas driven prophylaxis preparation dispensing system for attaching to a dental hand piece having an air/gas driven rotational member, said system comprising: (1) a disposable prophy angle comprised of a housing operatively supporting a gear train, said gear train having a posterior end removably attached to an air/gas driven rotational member of a dental hand piece to impart rotation of said gear train by the air/gas driven rotational member, and said gear train having a ventral end removably attached to a superior portion of said prophy cup, said prophy cup having a medial portion inferiorly transitioning into an outer peripheral wall having an inner surface defining an inner cavity, said medial portion having an opening extending therethrough and in open communication with said inner cavity of said prophy cup; (2) a prophylaxis preparation receptacle superiorly mounted on said disposable prophy angle, said prophylaxis preparation receptacle comprising an L-shaped passageway extending therethrough, said L-shaped passageway having an open entrance end, an open bend, and an open exit end generally perpendicular to said open entrance end, said L-shaped passageway containing a prophylaxis preparation; (3) a passageway extending from said open exit end of said L-shaped passageway, through a superior portion of said housing and a portion of said gear train, and to said opening in said medial portion of said prophy cup wherein said passageway provides open communication between said L-shaped passageway of said prophylaxis preparation receptacle and said inner cavity of said prophy cup; (4) a free piston disposed within said L-shaped passageway of said prophylaxis preparation receptacle between said open entrance end and said prophylaxis preparation; (5) receiving and diverting means for receiving air/gas pressure and adjustably diverting a portion of the air/gas pressure to drive said free piston toward said open exit end of said L-shaped passageway of said prophylaxis preparation receptacle for dispensing said prophylaxis preparation out of said open exit end, through said passageway, and out of said opening extending through said medial portion of said prophy cup to said internal cavity of said prophy cup while simultaneously driving said air/gas driven rotational member of said dental hand piece with a remaining portion of the air/gas pressure to impart rotation of said prophy cup while simultaneously dispensing the prophylaxis preparation into said internal cavity of said prophy cup.

Accordingly, it should be apparent that numerous modifications and adaptations may be resorted to without departing from the scope and fair meaning of the claims as set forth herein below following the detailed description of the invention.

DETAILED DESCRIPTION OF THE INVENTION

Considering the drawings, wherein like reference numerals denote like parts throughout the various drawing figures, reference numeral 10 is directed to an embodiment of an air/gas driven prophylaxis preparation dispensing system for a dental hand piece.

System Overview

Figure 1:
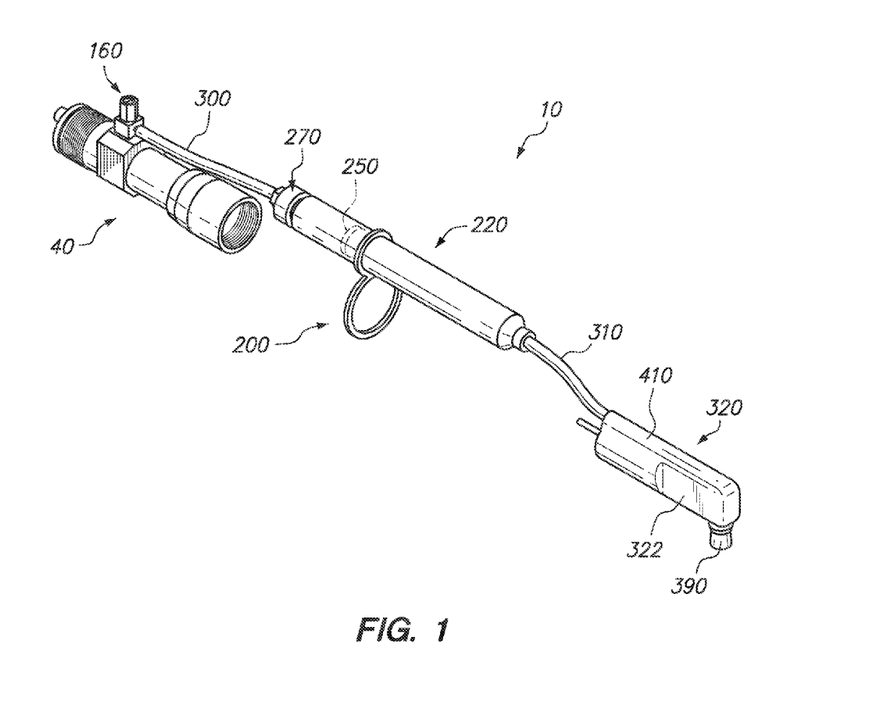
FIG. 1 is a top, front, and side perspective view of an embodiment of an air/gas driven prophylaxis preparation dispensing system.

Referring to FIG. 1, the air/gas driven prophylaxis preparation dispensing system 10 is comprised of a hand piece connector 40 comprising a superiorly mounted adjustable air/gas control valve 160, a prophylaxis preparation container assembly 220 having a free piston 250, and a disposable prophy angle assembly 320 comprising a disposable prophy angle 322 and a prophylaxis preparation receptacle 410 superiorly mounted thereon.

Figure 2:
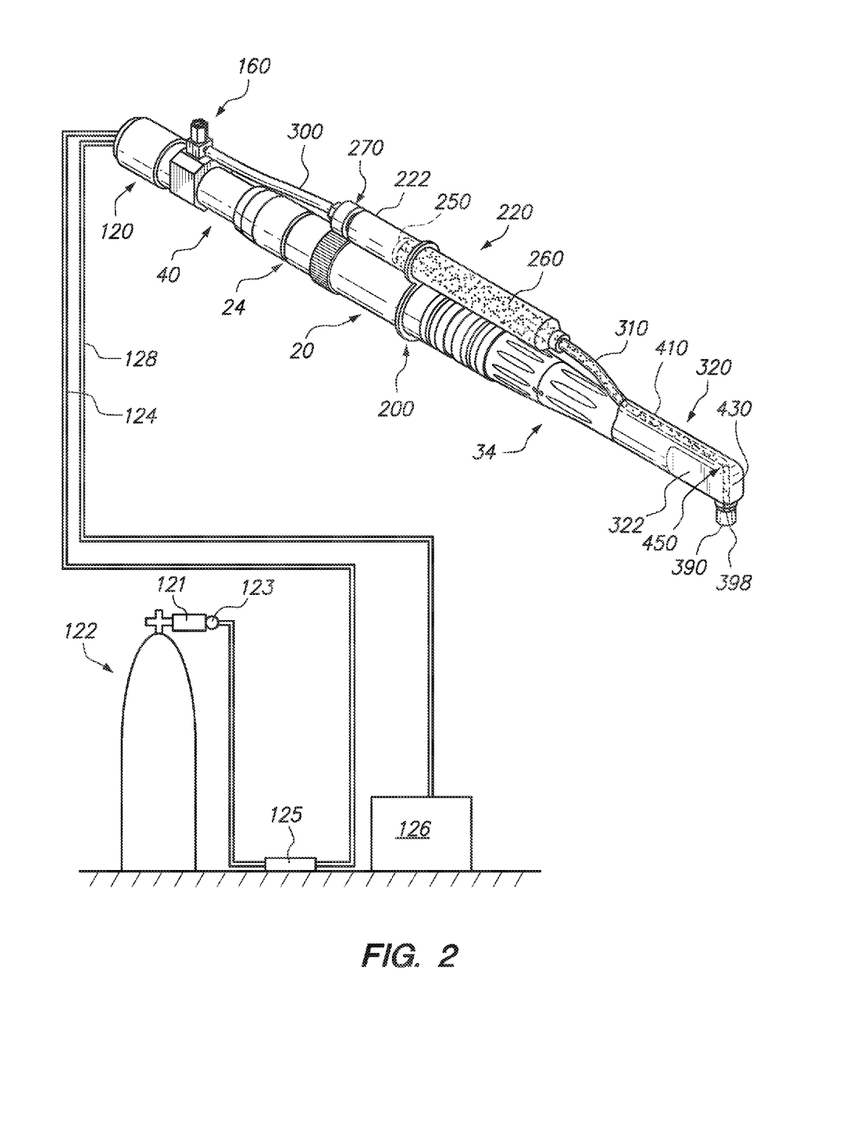
FIG. 2 is a top, front, and side perspective view of an embodiment of the air/gas driven prophylaxis preparation dispensing system shown operatively coupled to a dental hand piece and to an air/gas supply and exhaust system.

Referring to FIGS. 1 and 2, the hand piece connector 40 is operatively coupled between a posterior end portion 24 of a dental hand piece 20 and a conventional air/gas supply and exhaust system coupling 120 which, in turn, is operatively coupled to a conventional air/gas supply system 122 and an air/gas exhaust system 126 via dental tube 124, 128 respectively. The superiorly mounted adjustable air/gas control valve 160 is operatively coupled to the prophylaxis preparation container assembly 220 and controls air/gas flow to move a prophylaxis preparation 260 contained therein. In turn, the prophylaxis preparation container assembly 220 is operatively coupled the prophylaxis preparation receptacle 410 superiorly mounted on the disposable prophy angle 322. A disposable prophy cup 390 operatively couples to a ventral surface of the disposable prophy angle 322. The disposable prophy angle assembly 320 is operatively coupled to an anterior end portion 34 of the dental hand piece 20.

Still referring to FIGS. 1 and 2, and in general use and operation, a controllable flow of pressurized air/gas flows from the air/gas supply system 122 through the hand piece connector 40 and the superiorly mounted air/gas control valve 160 for supplying pressurized air/gas to drive the dental hand piece 20 and the disposable prophy angle 322 including the disposable prophy cup 390 while simultaneously supplying air/gas pressure to provide a continuous and controlled flow of the prophylaxis preparation 260 through the prophylaxis preparation container 222 and an L-shaped dispensing passageway 450 that is in open communication with at least one opening or orifice 398 in the prophy cup 390 such that the prophylaxis preparation 260 is deposited on an interior cleaning/polishing surface 402 (FIG. 10) of an interior cleaning/polishing cavity 404 of the rotating prophy cup 390 so that the prophylaxis preparation 260 can be applied onto a tooth or to teeth of a patient for polishing or cleaning regardless of the orientation of the disposable prophy cup 390 with respect the hand of the operator.

Dental Hand Piece 20

Figure 3:
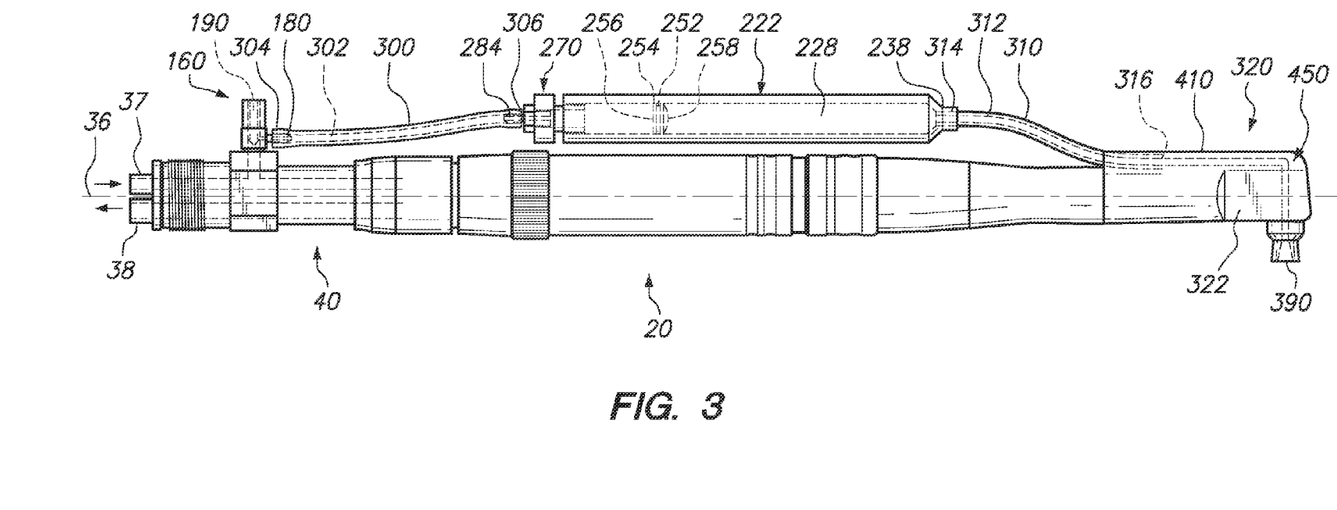
FIG. 3 is a side elevational view of an embodiment of the air/gas driven prophylaxis preparation dispensing system and of the dental hand piece.
Figure 4:
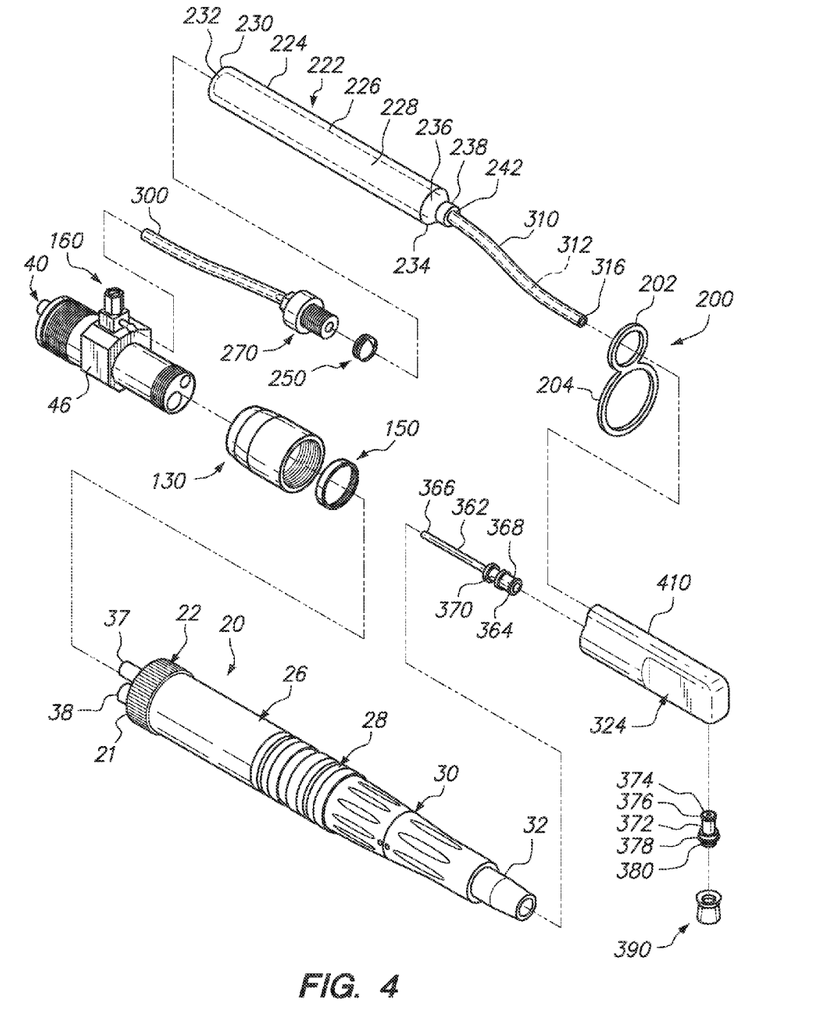
FIG. 4 is an exploded perspective view of an embodiment of the air/gas driven prophylaxis preparation dispensing system and a top, front, and side perspective view of the dental hand piece.

More specifically, and referring to FIGS. 3 and 4, the air/gas driven prophylaxis preparation dispensing system 10 is configured to operatively couple to a conventional dental hand piece 20. An embodiment of the dental hand piece 20 is comprised of, but is not limited to, a three-hundred-sixty degree quick connect swivel 22, a bidirectional motor piece 26 having a posterior end thereof operatively coupled to an anterior end of the quick connect swivel 22, an optional torque multiplier 28 having a posterior end thereof operatively coupled to an anterior end of the bidirectional motor piece 26, and a motor-to-angle adapter piece 30 having a posterior end thereof operatively coupled to an anterior end of the optional torque multiplier 28. In one embodiment, the attachment between the motor piece 26 and the optional torque multiplier 28 creates a secondary three-hundred-sixty degree quick connect swivel. The swivels are intended to reduce tubing drag, allow hand piece rotation to difficult areas of the mouth, and increase operator comfort. Additionally, the motor-to-angle adapter piece 30 comprises a conventional air/gas driven member 32 operatively coupled to and driven by bidirectional motor piece 26 which, in turn is driven by the air/gas that passes through the quick connect swivel 22 via inlet tube 37 and is exhausted via outlet tube 38. One specific manufacturer of the above delineated conventional dental hand piece 20 is sold under the trade name TITAN-T by STARDENTAL of Lancaster, Pa.

Hand Piece Connector 40 with Superiorly Mounted Air/Gas Control Valve 160

Figure 5:
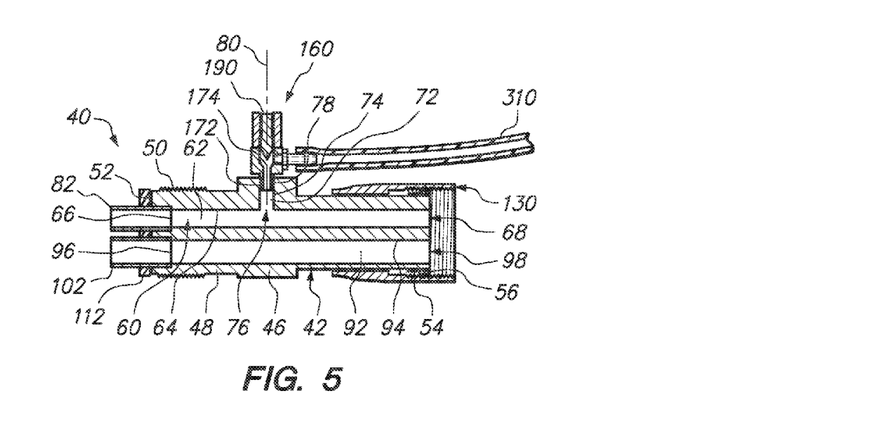
FIG. 5 is a side sectional view of an embodiment of a hand piece connector and superiorly mounted adjustable air/gas control valve of an embodiment of the air/gas driven prophylaxis preparation dispensing system.
Figure 6:
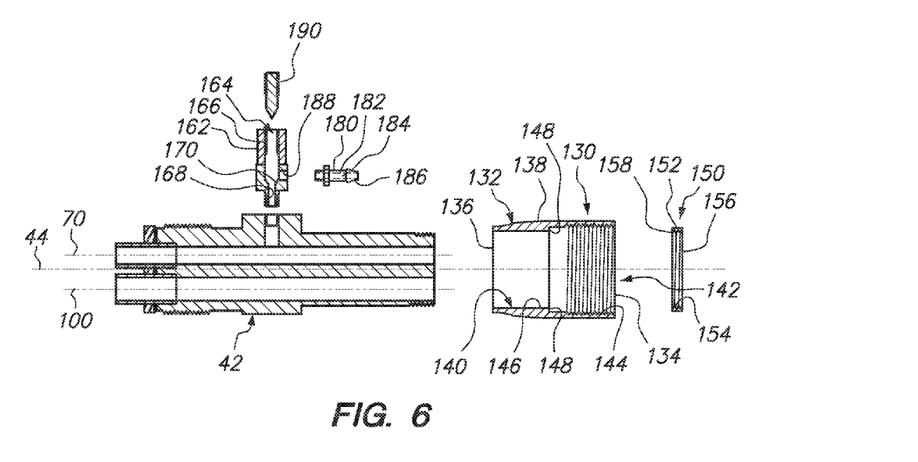
FIG. 6 is a partially exploded side sectional view of the hand piece connector and superiorly mounted adjustable air/gas control valve.

Now referring to FIGS. 5 and 6, the air/gas driven prophylaxis preparation dispensing system 10 is comprised of the hand piece connector 40 comprising the superiorly mounted adjustable air/gas control valve 160.

Hand Piece Connector 40

Specifically, the hand piece connector 40 is comprised of an elongated body 42 that has a central longitudinal axis 44 that is generally coincident with a central longitudinal axis 36 (FIG. 3) of the dental hand piece 20 when operatively coupled thereto. The elongated body 42 is generally cylindrically shaped with the exception of a faceted medial portion 46 radially extending away from a cylindrically shaped sidewall 48 of the elongated body 42. Additionally, the elongated body 42 is comprised of an exteriorly threaded posterior portion 50 disposed adjacent a posterior face 52 of the elongated body 42 and an exteriorly threaded anterior portion 54 disposed adjacent an anterior face 56 of the elongated body 42.

Extending through the elongated body 42 is an air/gas inlet passageway 60 and an air/gas return passageway 92.

The air/gas inlet passageway 60 has an inverted generally T-shaped configuration and is comprised of a first air/gas inlet passageway branch 62 defined by an interior, cylindrically shaped, first sidewall surface 64 extending through the elongated body 42 between a posterior open entrance end 66 extending through the posterior face 52 of the elongated body 42 and an anterior open end 68 extending through the anterior face 56 of the elongated body 42. The first air/gas inlet passageway branch 62 has a central longitudinal axis 70 that is generally parallel to the central longitudinal axis 44 of the elongated body 42.

Additionally, the air/gas inlet passageway 60 is comprised of an second air/gas inlet passageway branch 72 defined by an interior, cylindrically shaped, second sidewall surface 74 extending through the faceted medial portion 46 between an inferior open entrance end 76 extending through the first sidewall surface 64 and into open communication with the first air/gas inlet passageway branch 62 and a superior open end 78 extending through an exterior face of a facet of the faceted medial portion 46. The second air/gas inlet passageway branch 72 has a central longitudinal axis 80 that is generally perpendicular to the longitudinal axis 70 of the first air/gas inlet passageway branch 62 thereby defining the inverted T-shaped configuration of the air/gas inlet passageway 60.

An air/gas inlet tube insert 82 is frictionally or threadedly fitted within the posterior open entrance end 66 of the first air/gas inlet passageway branch 62. In one embodiment, the air/gas inlet tube insert 82 is in the form of a hollow cylindrical construct having an interior, cylindrically shaped, sidewall surface defining an air/gas inlet tube passageway extending therethrough, the passageway having a posterior open entrance end and an anterior open exit end in open communication with the first air/gas inlet passageway branch 62.

Furthermore, the elongated body 42 comprises an air/gas return passageway 92 defined by an interior, cylindrically shaped, third sidewall surface 94 extending through the elongated body 42 between a posterior open exit end 96 extending through the posterior face 52 of the elongated body 42 and an anterior open entrance end 98 extending through the anterior face 56 of the elongated body 42. The air/gas return passageway 92 has a central longitudinal axis 100 that is inferior and generally parallel to the central longitudinal axis 70 of the first air/gas inlet passageway 62 and to the central longitudinal axis 44 of the elongated body 42.

An air/gas return tube insert 102 is frictionally or threadedly fitted within the posterior open exit end 96 of the air/gas return passageway 92. In one embodiment, the air/gas return tube insert 102 is in the form of a hollow cylindrical construct having an interior, cylindrically shaped, sidewall surface defining an air/gas return tube passageway extending therethrough, the passageway having a posterior open exit end and an anterior open entrance end in open communication with the air/gas return passageway branch 92.

Moreover, a disk shaped gasket 112 abuts against the posterior face 52 of the elongated body 42 and comprises a pair of openings each at a complemental location for respectively receiving therethrough the air/gas inlet tube insert 82 and the air/gas return tube insert 102. This disk shaped gasket 112 forms a seal between the hand piece connector 40 and the conventional air/gas supply and exhaust system coupling 120 such that the air/gas inlet tube insert 82 is in open communication with the air/gas supply system 122 via dental tube 124 and the air/gas return tube insert 102 is in open communication with the exhaust system 126 via dental tube 128.

Hand Piece Sleeve 130 and Threaded Collar 150

The hand piece connector 40 is further comprised of a female hand piece connector sleeve 130 and a threaded collar 150 configured to operatively couple the hand piece connector 40 with the posterior end portion 24 (FIG. 1) of the conventional dental hand piece 20.

Specifically, and referring to FIG. 6, the female hand piece connector sleeve 130 is comprised of a stepped sleeve body 132 extending between an open anterior end 134 and an open posterior end 136. The stepped sleeve body 132 has a substantially smooth outer surface 138 and a stepped inner surface 140 that defines an open ended cylindrical central bore 142 that extends between the open anterior and posterior ends 134, 136 of the stepped sleeve body 132. The stepped inner surface 140 includes a circumscribing interiorly threaded surface portion 144 having a first inner diameter and posteriorly transitioning into an interior, substantially smooth, circumscribing surface 146 having second inner diameter that is less than the first inner diameter thereby forming an interior annular shoulder surface 148.

The threaded collar 150 includes an annular or ring shaped body 152 having a substantially smooth outer service and a threaded inner surface 154. The outer and inner surfaces extend between and are perpendicular with an anterior face 156 and a posterior face 158 of the ring shaped body 152.

Now referring again to FIGS. 5 and 6, the coupling the hand piece connector 40 to the dental hand piece 20 (FIG. 2) is initiated by passing the anterior face 56 of the elongated body 42 of connector 40 through the open posterior end 136 of the female hand piece connector sleeve 130 until the exteriorly threaded anterior portion 54 of the elongated body 42 is anteriorly beyond the open anterior end 134 of the female hand piece connector sleeve 130. Next, the threaded inner surface 154 of the threaded collar 150 is threadedly coupled to the exteriorly threaded anterior portion 54 of the elongated body 42 thereby allowing the female hand piece connector sleeve 130 to slide up to the threaded collar 150 while precluding the female hand piece connector sleeve 130 from slipping thereby. With the threaded collar 150 and the female hand piece connector sleeve 130 in place on the elongated body 42, a means for securing the elongated body 42 to the dental hand piece 20 is provided and accomplished by abutting the interior annular shoulder surface 148 of female hand piece connector sleeve 130 against the posterior face 158 of the ring shaped body 152 of the threaded collar 150 and threadedly engaging the interiorly threaded surface portion 144 of the stepped sleeve body 132 of female hand piece connector sleeve 130 with an exteriorly threaded posterior portion 21 (FIG. 4) of the three-hundred-sixty degree quick connect swivel 22 of the dental hand piece 20 so that the air/gas inlet tube 37 and the air/gas outlet tube 38 of the dental hand piece 20 are complementarily received within the first air/gas inlet passageway branch 62 and the air/gas return passageway 92 respectively and so that anterior face 156 of the ring shaped body 152 abuts against the posterior end of the three-hundred-sixty degree quick connect swivel 22. This coupling retains the ability of the dental hand piece 20 to swivel with respect to the air/gas supply and exhaust system coupling 120 (FIG. 2) via the three-hundred-sixty degree quick connect swivel 22.

Superiorly Mounted Air/Gas Control Valve 160

Still referring to FIGS. 5 and 6 and in light of the hand piece connector 40 described above, the superiorly mounted adjustable air/gas control valve 160 will now be described below.

The superiorly mounted adjustable air/gas control valve 160 is comprised of an air/gas control valve body 162 having a sideways oriented open ended T-shaped passageway 164 extending therethrough. The sideways (rotated ninety degrees counter clockwise) oriented T-shaped passageway 164 includes a top branch comprised of an interiorly threaded upper circumferential sidewall section 166 defining an upper superior passageway and an interior lower circumferential sidewall section 168 defining a lower superior passageway axially aligned and in open communication with the upper superior passageway. The lower superior passageway terminates into the second air/gas inlet passageway branch 72 thereby providing open communication between the second air/gas inlet passageway branch 72 and the T-shaped passageway 164. Accordingly, open communication is also provided between the T-shaped passageway 164 and the first air/gas inlet passageway branch 62. Additionally, the air/gas control valve body 162 is comprised of an inferiorly tapering axial seat 170 formed by a tapering diameter reduction in the interior lower circumferential sidewall section 168 of the T-shaped passageway 164.

Additionally, the superiorly mounted adjustable air/gas control valve 160 is comprised of an air/gas tube fitting 180 which is threadedly or frictionally fitted through a base branch of the T-shaped passageway 164 which is defined by an interiorly threaded circumferential medial sidewall section 188 at a location superiorly adjacent the inferiorly tapering axial seat 170 of the air/gas control valve body 162. The air/gas tube fitting 180 is comprised of an interior circumferential sidewall 182 defining an opened ended passageway 184 extending therethrough. The opened ended passageway 184 has a central longitudinal axis that is generally perpendicular relative to the central longitudinal axis 44 of the hand piece connector 40. The air/gas tube fitting 180 is also comprised of an anterior barbed end 186 that operatively couples to a flexible air/gas tube 300 as further described below.

The superiorly mounted adjustable air/gas control valve 160 is operatively coupled to the hand piece connector 40 via a nipple section 172 by being threadedly or frictionally coupled within passageway 72. Superiorly mounted adjustable air/gas control valve 160 may also be integrally formed with hand piece connector 40.

Additionally, the superiorly mounted adjustable air/gas control valve 160 is further comprised of a metering set screw 190 that passes through an open superior end of the upper superior passageway of the T-shaped passageway 164 and threadedly mates with the interiorly threaded upper circumferential sidewall section 166. The metering set screw 190 closes the upper superior passageway thereby forming a ninety degrees clockwise rotated L-shaped air/gas passageway 174 (FIG. 5) wherein the interior lower circumferential sidewall section 168 defines one branch of the L-shaped air/gas passageway 174, the location superiorly adjacent the inferiorly tapering axial seat 170 defines the bend of the L-shaped air/gas passageway 174, and the interior circumferential sidewall 182 of the air/gas tube fitting 180 defines the other branch of the L-shaped air/gas passageway 174.

Accordingly, the L-shaped air/gas passageway 174 provides open communication between the first air/gas inlet passageway branch 62 and the air/gas tube fitting passageway 184 which can be adjustably opened and closed via the metering screw 190.

Specifically, adjusting the metering set screw 190 in an inferior direction toward the inferiorly tapering axial seat 170 causes the metering set screw 190 to partially obstruct the L-shaped air/gas passageway 174 thereby reducing the amount of air/gas diverted from the first air/gas inlet passageway branch 62 into the air/gas tube fitting passageway 184 and on into the flexible air/gas tube 300. Conversely, adjusting the metering set screw 190 in a superior direction away from the inferiorly tapering axial seat 170 causes the metering set screw 190 to reduce the obstruction of the L-shaped air/gas passageway 174 thereby increasing the amount of air/gas diverted from the first air/gas inlet passageway branch 62 into the air/gas tube fitting passageway 184 and on into the flexible air/gas tube 300. When the metering setscrew 190 is seated with the inferiorly tapering axial seat 170, the L-shaped air/gas passageway 174 closes thereby shutting off or precluding air/gas from being diverted from the first air/gas inlet passageway branch 62 into the air/gas tube fitting passageway 184 and on into the flexible air/gas tube 300.

Accordingly, when air/gas is introduced from the air/gas supply system 122 to the first air/gas inlet passageway branch 62 via the air/gas inlet tube insert 82, a portion of the air/gas entering the first air/gas inlet passageway branch 62 is diverted to the flexible air/gas tube 300 by way of the superiorly mounted adjustable air/gas control valve 160 and, specifically, by way of the L-shaped air/gas passageway 174 having the diverted air/gas metered by use of the metering set screw 190. In one embodiment, the air/gas tube fitting 180 is in the form of a hose barb having barbed end 186 which attaches to an open posterior end 304 of the flexible air/gas tube 300 as shown in at least FIG. 5.

Prophylaxis Preparation Container Assembly 220

In general, and referring to FIGS. 1 and 4, the air/gas driven prophylaxis preparation dispensing system 10 is further comprised of the prophylaxis preparation container assembly 220. The prophylaxis preparation container assembly 220 is comprised of a prophylaxis preparation container 222, a free generally disk shaped cylindrical piston 250, an air/gas inlet tube coupling 270, and a prophylaxis preparation outlet tube 310

Figure 7:
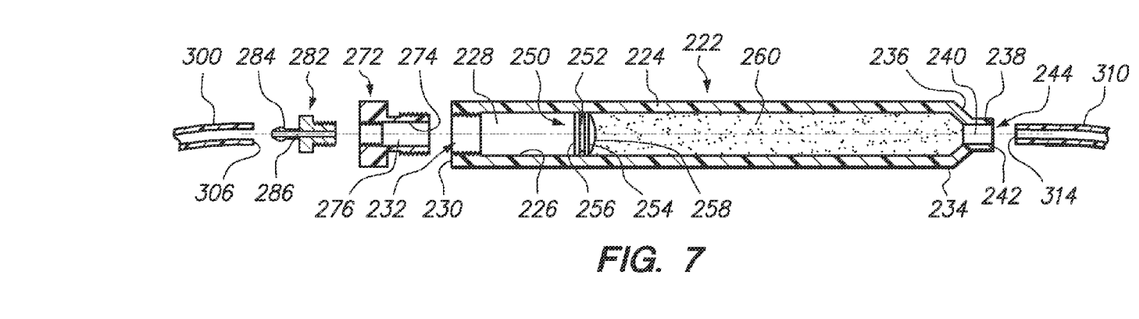
FIG. 7 is an exploded side sectional view of an embodiment of a prophylaxis preparation container assembly of an embodiment of the air/gas driven prophylaxis preparation dispensing system.
Figure 8:
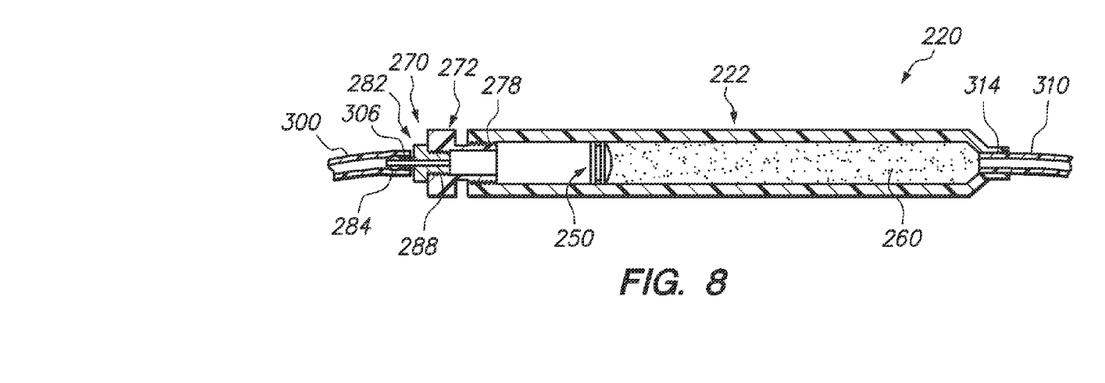
FIG. 8 is a side sectional view of the prophylaxis preparation container assembly.

Referring to FIGS. 4, 7, and 8, the prophylaxis preparation container 222 comprises a hollow cylindrical barrel 224 having an interior cylindrical surface 226 circumscribing an interior cylindrical cavity 228. The hollow cylindrical barrel 224 includes an annular posterior end 230 defining an annular posterior opening 232 of the interior cylindrical cavity 228. The hollow cylindrical barrel 224 further includes an annular anterior end 234 that transitions into a tapered anterior wall 236 which transitions into hollow anterior tip 238 having a tip passageway 240 extending therethrough and in open communication with the interior cylindrical cavity 228. The hollow anterior tip 238 terminates to an anterior tip end 242 having a reduced anterior tip or anterior exit opening 244 defining the anterior exit opening of the interior cylindrical cavity 228.

The prophylaxis preparation container 222 receives the free piston 250 through the annular posterior opening 232 of the hollow cylindrical barrel 224 wherein the free piston 250 is comprised of a disk shaped body 252 having an outer circumscribing periphery 254 and extending between a posterior face 256 and an anterior tapering face 258. The outer circumscribing periphery 254 of the disk shaped body 252 is configured to engage the interior cylindrical surface 226 of the hollow cylindrical barrel 224 in a fluid tight manner while being configured to slide longitudinally in the hollow cylindrical barrel 224 along a central longitudinal axis of the hollow cylindrical barrel 224 to expel a prophylaxis preparation 260 from the prophylaxis preparation container 222.

Specifically, the prophylaxis preparation 260 is contained within the prophylaxis preparation container 222 in a location between the anterior tapering face 258 of the free piston 250 and the complementary tapered anterior wall 236 of the hollow cylindrical barrel 224 and is dispensed from the interior cylindrical cavity 228 of the hollow cylindrical barrel 224 when an air/gas pressure is applied to the posterior face 256 of the free piston 250 via the superiorly mounted adjustable air/gas control valve 160. Accordingly, the volume of the interior cylindrical cavity 228 located between the anterior tapering face 258 of the free piston 250 and the complementary tapered anterior wall 236 of the hollow cylindrical barrel 224 defines a variable volume chamber containing a variable volume of prophylaxis preparation 260 when the free piston 250 is in motion.

Additionally, and as noted above, the prophylaxis preparation container assembly 220 is further comprised of an air/gas tube coupling 270, in one embodiment, the air/gas tube coupling 270 is comprised of a hollow bolt-shaped outer insert 272 and a hollow bolt-shaped inner insert 282.

The hollow bolt-shaped outer insert 272 is comprised of a posterior end transitioning into an exteriorly faceted head which, in turn, transitions into a shaft which terminates to an anterior end of the hollow bolt-shaped outer insert 272. The hollow bolt-shaped outer insert 272 is further comprised of an interior circumscribing sidewall 274 defining an open ended passageway 276 extending therethrough. As illustrated in FIG. 8, a threaded coupling 278 is formed between hollow bolt-shaped outer insert 272 and the prophylaxis preparation container 222.

The hollow bolt-shaped inner insert 282 is comprised of a posterior end posteriorly transitioning into a barbed posterior fitting 284 and anteriorly transitioning into an exteriorly faceted head which, in turn, transitions into a shaft that terminates to an anterior end of the hollow bolt-shaped inner insert 282. The hollow bolt-shaped inner insert 282 is further comprised of an interior passageway 286 extending therethrough. As illustrated in FIG. 8, a threaded coupling 288 is formed between the hollow bolt-shaped inner insert 282 and the hollow bolt-shaped outer insert 272.

Furthermore, and referring back to FIG. 3, the prophylaxis preparation container assembly 220 is further comprised of an air/gas inlet tube 300 and a prophylaxis preparation outlet tube 310. Both the air/gas inlet tube 300 and the prophylaxis preparation outlet tube 310 are, but not limited to, flexible plastic tubes.

The air/gas inlet tube 300 includes a passageway 302 extending therethrough, the passageway having an open posterior end 304 frictionally fitted onto the air/gas tube fitting or barb 180 of the superiorly mounted adjustable air/gas control valve 160 and an open anterior end 306 frictionally fitted onto the barbed fitting 284 of the air/gas tube coupling 270 thereby providing an open air/gas passageway between the superiorly mounted adjustable air/gas control valve 160 to the posterior face 256 of the free piston 250 slideably contained within the prophylaxis preparation container 222.

The prophylaxis preparation outlet tube 310 includes a passageway 312 extending therethrough, the passageway 312 having an open posterior end 314 frictionally fitted within the tip passageway 240 of the hollow tip 238 of the prophylaxis preparation container 222 and an open anterior end 316 frictionally fitted within a posterior end of an L-shaped passageway 416 of the superiorly mounted elongated prophylaxis preparation receptacle 410.

Disposable Prophy Angle Assembly 320

Referring now to FIGS. 1 through 4, the air/gas driven prophylaxis preparation dispensing system 10 is further comprised of the disposable prophy angle assembly 320 comprised of a disposable prophy angle 322 and a superiorly mounted prophylaxis preparation receptacle 410.

Disposable Prophy Angle 322

Figure 9:
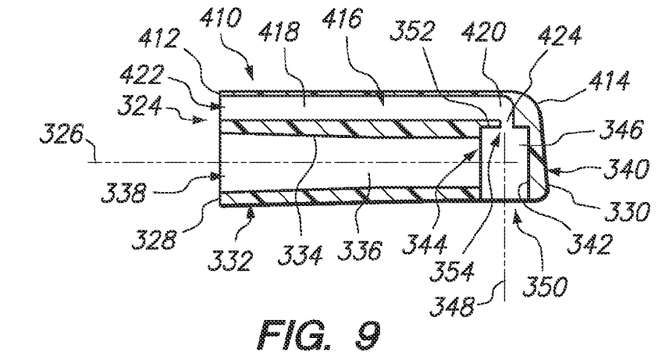
FIG. 9 is a side sectional view of an embodiment of a disposable prophy angle housing and a superiorly mounted prophylaxis preparation receptacle of an embodiment of the air/gas driven prophylaxis preparation dispensing system.
Figure 10:
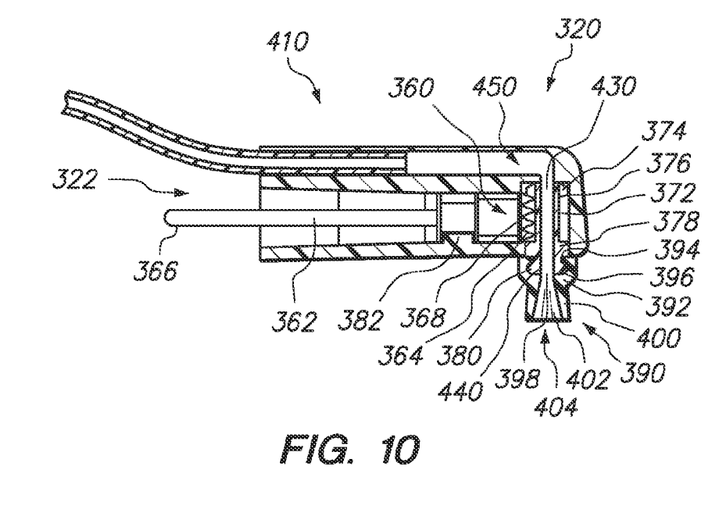
FIG. 10 is a side sectional view of an embodiment of a disposable prophy angle assembly of an embodiment of the air/gas driven prophylaxis preparation dispensing system.

More specifically, and referring to FIGS. 9 and 10, the disposable prophy angle 322 comprises a single or multi-piece elongated housing 324 having a longitudinal axis 326, a posterior end 328, and an anterior end 330. The elongated housing 324 is comprised of an elongated hollow sleeve member 332 that is in open communication with and transitions into a hollow head member 340. The hollow sleeve member 332 includes an interior circumscribing wall 334 that defines a central bore 336 that extends along the longitudinal axis 326 of elongated hollow sleeve member 332 from an open posterior end 338 of the hollow sleeve member 332 to an interior sidewall opening 344 in an interior sidewall 342 of the hollow head member 340.

The hollow head member 340 is generally at a right angle to the hollow sleeve member 332. The interior sidewall 342 of the hollow head member 340 defines a bore 346 that extends along a hollow head axis 348 that is generally perpendicular to the longitudinal axis 326 of the elongated housing 324. The bore 346 of the hollow head member 340 extends from an open inferior end or ventral opening 350 of the hollow head member 340 to a generally closed superior end 352 having an opening 354 extending therethrough and located superior to the interior sidewall opening 344 of the hollow head member 340.

Additionally, the disposable prophy angle assembly 320 is comprised of a gear train 360 which is operatively supported by the elongated housing 324 for transmitting rotational motion from the dental hand piece 20 to the disposable prophy cup 390.

Specifically, and referring to FIGS. 4, 9, and 10, the gear train 360 is comprised of an elongated drive shaft 362, a drive gear 364, a driven shaft 372, and a driven gear 374.

The elongated drive shaft 362 is at least partially disposed within the central bore 336 of the hollow sleeve member 332 and includes a posterior end 366 operatively coupled to an air/gas driven member 32 of the dental hand piece 20 to impart rotation of the elongated drive shaft 362. The drive gear 364 is connected to an anterior end 368 of the elongated drive shaft 362 and is at least partially disposed within the bore 346 of the hollow head member 340 via, the interior sidewall opening 344.

The driven shaft 372 is at least partially disposed within the bore 346 of the hollow head member 340 and includes a superior end 376 and an inferior end 378. The driven gear 374 is disposed within the bore 346 of the hollow head member 340 and is connected to the superior end 376 of the driven shaft 372 in meshing engagement with the drive gear 364 for rotating the driven gear 374 about axis 348 generally perpendicular to the longitudinal axis 326 of the elongated housing 324. A boss 380 is disposed below the ventral opening 350 of the hollow head member 340 and is connected to the inferior end 378 of the driven shaft 372, in turn, the disposable prophy cup 390 is operatively mounted to the boss 380 in a conventional manner.

In one embodiment, a tab 382 is located through the hollow sleeve member 332 and locks into a rim 370 of the elongated drive shaft 362 to preclude the elongated drive shaft 362 and connected drive gear 364 from sliding out of the hollow sleeve member 332 which, in turn, precludes the driven shaft 372 and the connected driven gear 374 from sliding out of the hollow head member 340.

Disposable Prophy Cup 390 with Opening 398

In one embodiment, the disposable prophy cup 390 is a standard commercially available design that has been modified to include at least one top or medial body opening 398 within the prophy cup 390 for providing open communication with the interior polishing/cleaning cavity 404 and interior polishing/cleaning surface 402 of the prophy cup 390.

Specifically, the disposable prophy cup 390 is comprised of a body portion 392 having an interiorly and outwardly extending sidewall 400 depending therefrom. The body portion 392 includes a superior upper body opening 394 that inferiorly transitions into a boss profiled cavity 396 which, in turn, inferiorly transitions into the top or medial body opening 398 within the prophy cup 390. The sidewall 400 inferiorly and outwardly extends from a location adjacent the top or medial body opening 398 of body portion 392 and includes the interior polishing/cleaning surface 402 defining the interior polishing/cleaning cavity 404 disposed directly below and in open communication with the top or medial body opening 398 within the prophy cup 390.

Accordingly, the disposable prophy cup 390 is operatively mounted to the boss 380 in the conventional manner of pressing the boss through the superior upper body opening 394 and into the boss profiled cavity 396.

Superiorly Mounted Receptacle 410

Referring to FIGS. 9 and 10, the disposable prophy angle assembly 320 is further comprised of a superiorly mounted elongated prophylaxis preparation receptacle 410. The superiorly mounted elongated prophylaxis preparation receptacle 410 is attached to or integrally formed with the superior surface of the elongated housing 324 of the disposable prophy angle 322 and includes a posterior end 412 located adjacent the posterior end 328 of the disposable prophy angle 322 and an anterior end 414 located just anteriorly beyond the opening 354 extending through the generally closed superior end 352 of the hollow head member 340 of the disposable prophy angle 322.

Additionally, the superiorly mounted elongated prophylaxis preparation receptacle 410 comprises a generally L-shaped passageway 416 extending therethrough. The L-shaped passageway 416 includes a first passageway branch 418 extending between a passageway branch bend 420 and an open posterior end 422 adjacent the posterior end 412 of the receptacle 410. In turn, a second passageway branch 424 of the L-shaped passageway 416 extends between the passageway branch bend 420 and an open inferior end defined by the opening 354 extending through the generally closed superior end 352 of the hollow head member 340 of the disposable prophy angle 322. Generally, the passageway branch bend 420 is at an angle of generally ninety degrees when the hollow head member 340 extends at an angle of generally ninety degrees with respect to the hollow sleeve member 332. If the hollow head member 340 extends at an acute or obtuse angle with respect to the hollow sleeve member 332, then the passageway branch bend 420 would have a complemental acute or obtuse bend respectively.

Referring to FIG. 10, and as an extension of the second passageway branch 424 and opening 354 illustrated in FIG. 9, an open ended central passageway 430 extends through the driven gear 374, the driven shaft 372, and the boss 380. Central passageway 430 includes an open superior entrance end that is in open communication with the second passageway branch 424 and an open inferior exit end that is in open communication with interior polishing/cleaning cavity 404 of the disposable prophy cup 390 via the top or medial body opening 398. In one embodiment, an open ended hollow metal tube insert 440 extends through the driven gear 374, the driven shaft 372, and the boss 380 and includes a passageway that defines the central passageway 430.

Accordingly, and referring to FIGS. 9 and 10, an open ended L-shaped dispensing passageway 450 is defined by L-shaped passageway 416 extending through the superiorly mounted elongated prophylaxis preparation receptacle 410 and the central passageway 430 that extends through the driven gear 374, the driven shaft 372, and the boss 380 for providing a prophylaxis preparation flow path to the interior polishing/cleaning cavity 404 of the disposable prophy cup 390 for allowing the prophylaxis preparation 260 that is forced from the prophylaxis preparation container 222 to flow through the L-shaped dispensing passageway 450 and into the interior polishing/cleaning cavity 404 and onto the interior polishing/cleaning surface 402 of the disposable prophy cup 390 so that the prophylaxis preparation 260 can be applied onto a tooth or to teeth for polishing or cleaning regardless of the orientation the disposable prophy cup 390 with respect the hand of the operator.

In Use and Operation

In use and operation, and referring to FIGS. 1 through 7, one end of the conventional air/gas supply and exhaust coupling 120 is operatively coupled to the air/gas supply system 122 and the air/gas exhaust systems 126 while the opposing end of coupling 120 is removeably coupled to a posterior end of hand piece connector 40. In turn, the hand piece connector 40 with the superiorly mounted adjustable air/gas control valve 160 to the posterior end portion 24 of dental hand piece 20 and swivels therewith via the three-hundred-sixty degree quick connect swivel 22. The superiorly mounted air/gas control valve 160 is operatively coupled to the prophylaxis preparation container assembly 220 as delineated above. A double ring coupling 200 comprised of a prophylaxis preparation container ring 202 and a hand piece ring 204 is utilized to couple the prophylaxis preparation container assembly 220 to the hand piece 20 as illustrated in FIG. 2.

The anterior end portion 34 of the dental hand piece 20 is operatively coupled to the disposable prophy angle assembly 322 via the removable coupling or attachment of the posterior end 366 of the gear train 360 with the air/gas driven rotational member 32 driven by the bidirectional motor piece 26 via an optional torque multiplier 28 thereby imparting rotation of the gear train 360 in response to air/gas from the air/gas supply system 122 passing through tubing 124, coupling 120, and hand piece connector 40 and driving the bidirectional motor piece 26 thereby rotating the air/gas driven rotational member 32 via the optional torque multiplier 28 which, in turn, imparts rotation of the ventral end or boss 380 and the removably attached disposable prophy cup 390.

The superiorly mounted prophylaxis preparation container 222 is operatively coupled to the prophylaxis container receptacle 410 which is contained on the superior aspect of the disposable prophy angle 322. Accordingly, and as described above, a portion of the air/gas that is supplied to the hand piece connector 40 flows therethrough to drive, in a conventional manner, the dental hand piece 20 and the disposable prophy angle 322 which, in turn, rotates the disposable prophy cup 390 in a conventional manner. Simultaneously, a portion of the air/gas that is supplied to the hand piece connector 40 is diverted through the adjustable air/gas control valve 160 for providing an adjustable air/gas flow. The adjustable air/gas flow drives the prophylaxis preparation 260 through the prophylaxis preparation container 222 to the prophylaxis preparation container receptacle 410. The prophylaxis preparation 260 then exhibits a continued controlled flow through the L-shaped dispensing passageway 450 in the disposable prophy angle assembly 320, through the top or medial body opening 398 of the disposable prophy cup 390, and into the interior polishing/cleaning cavity 404 of the disposable prophy cup 390 so that the prophylaxis preparation 260 can be applied onto a tooth or to teeth for polishing or cleaning regardless of the orientation the disposable prophy cup 390 with respect the hand of the operator.

In one embodiment, air/gas flow from the air/gas supply system 122 is regulated by a conventional regulator 121 and measured by a conventional pressure gauge 123. Additionally, a foot controller 125 is typically provided to allow for variable control of the air/gas flow from the air/gas supply system 122 to the hand piece connector 40 as a function of foot pressure of the operator.

Although the air/gas driven prophylaxis preparation dispensing system 10 is illustrated as being operatively coupled to the dental handpiece 20, it is intended in another aspect that the system 10 be utilized generally on other handpieces and configuration thereof.

Figure 11:
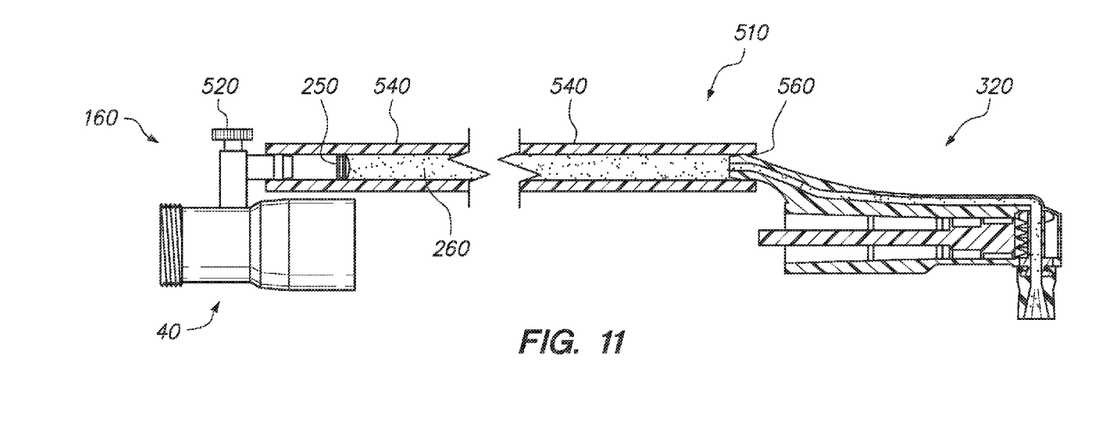
FIG. 11 is a partial side sectional view of another embodiment of the air/gas driven prophylaxis preparation dispensing system.

In another aspect, an embodiment of the invention illustrated in FIG. 11 utilizes a thumb head type of set screw 490 as an alternative to the recessed metering set screw 190. Additionally, an embodiment of the invention illustrated in FIG. 11 utilizes an elongated prophylaxis preparation tube 520 in place of the prophylaxis preparation container assembly 220 while retaining free piston 250. Furthermore, an embodiment of the invention illustrated in FIG. 11 utilizes a barbed end extension 540 of the posterior end 412 of the superiorly mounted prophylaxis preparation receptacle 410.

Figure 12:
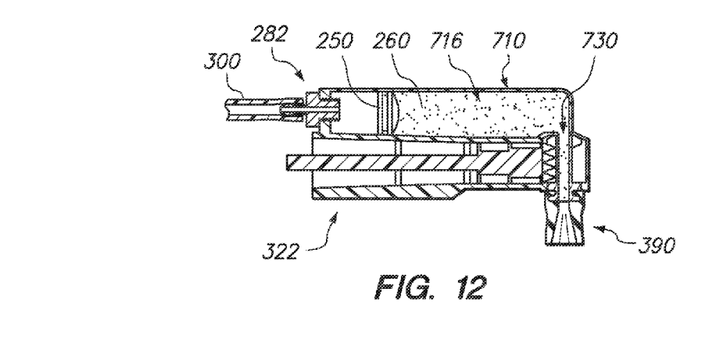
FIG. 12 is a side sectional view of a further embodiment of the air/gas driven prophylaxis preparation dispensing system.

In a further aspect, and referring to FIG. 12 and generally to FIGS. 1 through 10 as required, an embodiment of the invention provides an air/gas driven prophylaxis preparation dispensing system 710 for attaching to the dental hand piece 20 having the air/gas driven rotational member 32, said system comprising: (1) a disposable prophy angle 322 comprised of a housing operatively supporting a gear train, said gear train having a posterior end removably attached to an air/gas driven rotational member 32 of a dental hand piece 20 to impart rotation of said gear train by the air/gas driven rotational member, and said gear train having a ventral end removably attached to a superior portion of said prophy cup 390, said prophy cup having a medial portion inferiorly transitioning into an outer peripheral wall having an inner surface defining an inner cavity, said medial portion having an opening extending therethrough and in open communication with said inner cavity of said prophy cup; (2) a prophylaxis preparation receptacle 710 superiorly mounted on said disposable prophy angle, said prophylaxis preparation receptacle comprising an L-shaped passageway 716 extending therethrough, said L-shaped passageway having an open entrance end, an open bend, and an open exit end generally perpendicular to said open entrance end, said L-shaped passageway containing a prophylaxis preparation 260; (3) a passageway 730 extending from said open exit end of said L-shaped passageway, through a superior portion of said housing and a portion of said gear train, and to said opening in said medial portion of said prophy cup wherein said passageway provides open communication between said L-shaped passageway of said prophylaxis preparation receptacle and said inner cavity of said prophy cup; (4) a free piston 250 disposed within said L-shaped passageway of said prophylaxis preparation receptacle between said open entrance end and said prophylaxis preparation; (5) receiving and diverting means (hand piece connector 40, superiorly mounted adjustable air/gas control valve 160, air/gas tube 300, and hollow bolt shaped inner insert 282) for receiving air/gas pressure and adjustably diverting a portion of the air/gas pressure to drive said free piston toward said open exit end of said L-shaped passageway of said prophylaxis preparation receptacle for dispensing said prophylaxis preparation out of said open exit end, through said passageway, and out of said opening extending through said medial portion of said prophy cup to said internal cavity of said prophy cup while simultaneously driving said air/gas driven rotational member of said dental hand piece with a remaining portion of the air/gas pressure to impart rotation of said prophy cup while simultaneously dispensing the prophylaxis preparation into said internal cavity of said prophy cup.

The above delineation of the system 10, including its methods and aspects demonstrate the industrial applicability of this invention.

Moreover, it should be apparent that numerous modifications and adaptations may be resorted to without departing from the scope and fair meaning of this invention as set forth hereinabove and as described herein below by the claims.

We claim:

1. An air/gas driven prophylaxis preparation dispensing system for attaching to a dental hand piece having an air/gas driven rotational member, said system comprising:

a disposable prophy angle comprised of a housing operatively supporting a gear train, said gear train having a posterior end configured for removably attaching to an air/gas driven rotational member of the dental hand piece to impart rotation of said gear train, and said gear train having a ventral end removably attached to a superior portion of a prophy cup, said prophy cup having a medial portion inferiorly transitioning into an outer peripheral wall having an inner surface defining an inner cavity, said medial portion having an opening extending therethrough and in open communication with said inner cavity of said prophy cup;

a prophylaxis preparation receptacle superiorly mounted on said disposable prophy angle, said prophylaxis preparation receptacle having an open posterior end;

a passageway in open communication with said open posterior end of said prophylaxis preparation receptacle and extending through said prophylaxis preparation receptacle, a superior portion of said housing, and a portion of said gear train to said opening in said medial portion of said prophy cup wherein said passageway provides open communication between said prophylaxis preparation receptacle and said inner cavity of said prophy cup;

a prophylaxis preparation container having a cavity containing a prophylaxis preparation and having an open entrance end and an opposing open delivery end in open communication with said cavity;

a free piston disposed within said cavity between said open entrance end and said prophylaxis preparation;

a prophylaxis preparation outlet tube operatively coupled between said open delivery end of said prophylaxis preparation container and said open posterior end of said prophylaxis preparation receptacle for providing open communication between said cavity containing the prophylaxis preparation and said passageway;

receiving and diverting means for receiving an air/gas pressure and adjustably diverting a portion of the air/gas pressure to drive said free piston toward said open delivery end of said prophylaxis preparation container for dispensing said prophylaxis preparation out of said open delivery end, through said prophylaxis preparation outlet tube and said passageway, and out of said opening extending through said medial portion of said prophy cup to said internal cavity of said prophy cup while simultaneously driving said air/gas driven rotational member of said dental hand piece with a remaining portion of the air/gas pressure to impart rotation of said prophy cup while simultaneously dispensing the prophylaxis preparation into said internal cavity of said prophy cup; wherein said receiving and diverting means is comprised of a hand piece connector and an adjustable air/gas control valve superiorly mounted on said hand piece connector, said hand piece connector having an elongated body having a central longitudinal axis generally perpendicular to a central longitudinal axis of said adjustable air/gas control valve and configured for removably attaching to the hand piece for having said central longitudinal axis coincident with a central longitudinal axis of the hand piece.

2. The system of claim 1 wherein said elongated body of said hand piece connector includes a bifurcated air/gas inlet passageway having a first branch operatively coupled between an air/gas supply system and the hand piece and an air/gas return passageway operatively coupled between the hand piece and an air/gas exhaust system.

3. The system of claim 2 wherein said bifurcated air/gas inlet passageway is further comprised of a second branch in open communication with said first branch and operatively coupled to a ninety degrees clockwise rotated L-shaped passageway extending through said superiorly mounted adjustable air/gas control valve.

4. The system of claim 3 wherein said superiorly mounted adjustable air/gas control valve is comprised of a metering set screw operatively coupled within in a bend of said L-shaped passageway for adjustably opening and closing said L-shaped passageway for metering the portion of the air/gas pressure that drives said free piston toward said open delivery end of said prophylaxis preparation container for controlling the dispensing of said prophylaxis preparation out of said open delivery end, through said prophylaxis preparation outlet tube and said passageway, and out of said opening extending through said medial portion of said prophy cup to said internal cavity of said prophy cup.

5. The system of claim 4 wherein said metering set screw is threadedly mated within a threaded passageway disposed within said superiorly mounted adjustable air/gas control valve wherein said threaded passageway is aligned with and superior to said bend of said L-shaped passageway.

6. The system of claim 5 wherein said metering set screw is rotated in a first direction about said central longitudinal axis of said adjustable air/gas control valve to adjustably close said L-shaped passageway and in a second direction opposite said first direction to adjustably open said L-shaped passageway.

7. An air/gas driven prophylaxis preparation dispensing system for attaching to a dental hand piece having an air/gas driven rotational member, said system comprising:

a disposable prophy angle housing comprising a hollow sleeve member having an open posterior end and a hollow head member formed at an anterior end of said hollow sleeve member, said hollow head member having a ventral opening;

a drive shaft partially disposed within said hollow sleeve member and having a posterior end portion configured for operatively coupling to an air/gas driven rotational member of the dental hand piece to impart rotation of said drive shaft by the air/gas driven rotational member;

a drive gear partially disposed within said hollow head member and attached to an anterior end portion of said drive shaft;

a driven shaft disposed within said hollow head member and having a superior end portion and an inferior end portion, said inferior end portion having a boss extending below said ventral opening of said hollow head member;

a driven gear disposed within said hollow head member and attached to said superior end portion of said driven shaft, said driven gear operatively meshed with said drive gear to have rotation imparted to said driven gear by said drive gear operatively coupled to the air/gas driven rotational member;

a prophylaxis preparation receptacle superiorly mounted on said disposable prophy angle housing, said prophylaxis preparation receptacle having an open posterior end;

a passageway in open communication with said open posterior end of said prophylaxis preparation receptacle extending through said prophylaxis preparation receptacle, said driven shaft, and said boss, said passageway having an open entrance end in a posterior end of said prophylaxis preparation receptacle and an open dispensing end in said boss;

a prophy cup operatively coupled to said boss and extending below said ventral opening of said hollow head member, said prophy cup having an internal cavity and an opening interposed between and in open communication with said internal cavity and said open dispensing end in said boss;

a prophylaxis preparation container having a cavity containing a prophylaxis preparation and having an open entrance end and an opposing open delivery end in open communication with said cavity;

a free piston disposed within said cavity between said open entrance end and said prophylaxis preparation;

a prophylaxis preparation outlet tube operatively coupled between said open delivery end of said prophylaxis preparation container and said open posterior end of said prophylaxis preparation receptacle for providing open communication between said cavity containing the prophylaxis preparation and said passageway;

receiving and diverting means for receiving air/gas pressure and adjustably diverting a portion of the air/gas pressure to drive said free piston toward said open delivery end of said prophylaxis preparation container for dispensing said prophylaxis preparation out of said open delivery end, through said prophylaxis preparation outlet tube and said passageway, through said open dispensing end in said boss, and out of said opening of said prophy cup to said internal cavity of said prophy cup while simultaneously driving said air/gas driven rotational member of said dental hand piece with a remaining portion of the air/gas pressure to impart rotation of said prophy cup; wherein said receiving and diverting means is comprised of a hand piece connector and an adjustable air/gas control valve superiorly mounted on said hand piece connector, said hand piece connector having an elongated body having a central longitudinal axis generally perpendicular to a central longitudinal axis of said adjustable air/gas control valve and configured for removably attaching to the hand piece for having said central longitudinal axis coincident with a central longitudinal axis of the hand piece.

8. The system of claim 7 wherein said elongated body of said hand piece connector includes a bifurcated air/gas inlet passageway having a first branch operatively coupled between an air/gas supply system and the hand piece and an air/gas return passageway operatively coupled between the hand piece and an air/gas exhaust system.

9. The system of claim 2 wherein said bifurcated air/gas inlet passageway is further comprised of a second branch in open communication with said first branch and operatively coupled to a ninety degrees clockwise rotated L-shaped passageway extending through said superiorly mounted adjustable air/gas control valve.

10. The system of claim 2 wherein said superiorly mounted adjustable air/gas control valve is comprised of a metering set screw operatively coupled within in a bend of said L-shaped passageway for adjustably opening and closing said L-shaped passageway for metering the portion of the air/gas pressure that drives said free piston toward said open delivery end of said prophylaxis preparation container for controlling the dispensing of said prophylaxis preparation out of said open delivery end, through said prophylaxis preparation outlet tube and said passageway, and out of said opening extending through said medial portion of said prophy cup to said internal cavity of said prophy cup.

11. The system of claim 3 wherein said metering set screw is threadedly mated within a threaded passageway disposed within said superiorly mounted adjustable air/gas control valve wherein said threaded passageway is aligned with and superior to said bend of said L-shaped passageway.

12. The system of claim 4 wherein said metering set screw is rotated in a first direction about said central longitudinal axis of said adjustable air/gas control valve to adjustably close said L-shaped passageway and in a second direction opposite said first direction to adjustably open said L-shaped passageway.

\* \* \* \* \*